United States Patent [19]

Stroupe et al.

[11] 4,200,435

[45] Apr. 29, 1980

[54] DETERMINATION OF GLYCOSYLATED HEMOGLOBIN IN BLOOD

[75] Inventors: Stephen D. Stroupe; Edwin G. Moore, both of Libertyville, Ill.

[73] Assignee: Abbott Laboratories, North Chicago, Ill.

[21] Appl. No.: 973,368

[22] Filed: Dec. 26, 1978

[51] Int. Cl.$^2$ ............... G01N 33/16; G01N 21/00
[52] U.S. Cl. ............... 23/230 B; 252/408; 356/39
[58] Field of Search ............... 23/230 B; 252/408; 356/39

[56] References Cited

U.S. PATENT DOCUMENTS

| | | | |
|---|---|---|---|
| 3,918,905 | 11/1975 | Warren | 252/408 X |
| 3,958,560 | 5/1976 | March | 356/39 X |
| 3,964,865 | 6/1976 | Das | 252/408 X |
| 4,077,772 | 3/1978 | Geissler | 252/408 X |
| 4,142,858 | 3/1979 | Acuff | 23/230 B |

OTHER PUBLICATIONS

M. J. McDonald et al., J. Biol. Chem., 254(3), 702–707 (1979).
M. F. Perutz, Scientific American, 239(6), 92–125 (Dec. 1978).
Ruth E. Benesh et al., Advances in Protein Chemistry, vol. 28, 211–237 (1974).
H. F. Bunn et al., Science, 200, 21–27 (Apr. 1978).
M. F. Perutz et al., Biochemistry, 17(17), 3640–3652 (1978).
S. J. Edelstein, Annual Review of Biochemistry, vol. 44, 209–232 (1975).
R. G. Shulman et al., Quat. Rev. Biophysics, 8(3), 325–420 (1975).

*Primary Examiner*—Sidney Marantz
*Attorney, Agent, or Firm*—John J. McDonnell

[57] ABSTRACT

A method for determining glycosylated hemoglobin in blood samples which involves liberating hemoglobins from red blood cells by chemical or physical means and reacting non-glycosylated hemoglobin with an allosteric site binding substance which reacts with the allosteric binding site of non-glycosylated hemoglobin and thereby alters the distribution between allosteric forms of the hemoglobins and measuring the change. This method is useful in monitoring glucose metabolism for detecting and controlling diabetes.

6 Claims, No Drawings

DETERMINATION OF GLYCOSYLATED HEMOGLOBIN IN BLOOD

BACKGROUND OF THE INVENTION

Hemoglobin exists in two allosteric forms. The T (taught) and the R (relaxed) form. These forms have different chemical and physical properties and the relative amounts of R and T hemoglobin can be determined by art recognized techniques such as ultraviolet, infrared, visible, nuclear magnetic resonance, and electron spin resonance spectroscopy. For example, Perutz et al., Biochem., No. 17, 3641 (1978) describes absorption spectra of hemoglobin derivatives, i.e., R→T transition as a function of ligand and inositol hexaphosphate binding. Circular dichroism and chemical reactivity are among other techniques for distinguishing R and T states of hemoglobin. The relative amount of R and T states can be determined by both end-point and kinetic techniques.

Elevated levels of glycosylated hemoglobin are known to be associated with diabetes mellitus. Glycosylated hemoglobin is present in non-diabetics at a level of about 5% of total hemoglobin, while diabetics have 2–4 times that amount (Science, 200, Apr. 7, 1978). Glycosylated hemoglobin level provides an index of a patient's average blood glucose concentration over a long period of time. This index is not affected by short-term fluctuations in blood sugar (hour-to-hour) and, hence, gives a relatively precise reflection of the state of blood glucose control in diabetics.

Glycosylated hemoglobin is commonly referred to as HbA or fast hemoglobin because it migrates faster on a chromatograph column and, indeed, is generally measured by chromatography or electrophoresis.

It has been discovered that the percent of glycosylated hemoglobin in blood can be measured by monitoring the shift in the equilibrium populations of R and T allosteric forms of hemoglobins when the non-glycosylated hemoglobin is reacted with an allosteric site binding substance. This reaction causes a shift from the R to the T allosteric form in the non-glycosylated fraction portion of the hemoglobin. The glycosylated hemoglobin in the blood sample does not contribute to the shaft in the equilibrium of the allosteric forms since glycosylation blocks the allosteric binding site. Thus, the higher the percentage of glycosylated hemoglobin in the blood sample, the smaller the shift between allosteric forms upon reacting the hemoglobins with an allosteric site binding substance. The present invention takes advantage of the reactivity of the allosteric binding site which is accessible in non-glycosylated hemoglobin and the resulting shift in the equilibrium of allosteric forms of the glycosylate and non-glycosylated hemoglobin mixture resulting when an allosteric binding site substance is reacted with the non-glycosylated hemoglobin fraction.

SUMMARY OF THE INVENTION

The present invention encompasses a method for determining glycosylated hemoglobin in blood samples which involves liberating hemoglobins from red blood cells by chemical or physical means and reacting non-glycosylated hemoglobin with an allosteric site binding substance which reacts with the allosteric binding site of non-glycosylated hemoglobin and thereby alters the distribution between allosteric forms of the hemoglobins and measuring the change. Unexpectedly, the present invention provides methods and reagents for a clinical assay of glycosylated hemoglobin in blood samples.

DETAILED DESCRIPTION OF THE INVENTION

A wide variety of compounds are known as effective allosteric effector site binding substances. These include organophosphates, sulfates, carboxylic acids represented by inositol hexaphosphate, J. Biol. Chem., 246, 7168 (1971); 2,3-diphosphoglycerate, Nature, 234, 174 (1971); adenosine triphosphate, Biochem. Biophys. Res. Comm., 26, 162 (1967); pyridoxal phosphate, Fed. Proc. Fed. Amer. Soc., Expl. Biol., 28, 604 (1969); inositol hexasulfate, Biochemistry, 15, 3396 (1976); inositol pentaphosphate, Can. J. Chem., 47, 63 (1969); 8-hydroxy-1,3,6-pyrenetrisulfonate, J. Biol. Chem., 246, 5832 (1971); O-iodosodium benzoate, The Journal of Pharmacology and Experimental Therapeutics, 203, 72 (1977). Those skilled in the hemoglobin arts will recognize a wide variety of effector site binding substances equivalent for practicing the present invention. Inositol hexaphosphate is a preferred allosteric effector site binding substance.

It is generally desirable to lyse red blood cells to release hemoglobins. Common cationic (e.g., cetyl trimethyl ammonium bromide); anionic (e.g., sodium dodecylsulfate and sodium deoxycholate) and neutral (e.g., saponin and octyl phenoxypolyethoxyethanol) detergents are useful in lysing red blood cells. Neutral detergents in the concentration range of about 0.025 to 0.5 volume percent are preferred. Mechanical rupture, for example ultrasonication and hypotonic lysis, are also effective ways of releasing hemoglobin from red blood cells.

Binding of heme-binding ligands to heme iron generally shifts the equilibrium of allosteric hemoglobin isomers to the relaxed (R) form. Thus, when the heme-binding moiety of the hemoglobins in the test sample is coordinated with a heme-binding ligand larger shifts in the equilibrium populations of allosteric forms of hemoglobin are observed. This magnification in shift in equilibrium enhances accuracy and precision of glycosylated hemoglobin determination. This coordination of heme-binding ligand to shift equilibrium of allosteric isomers is applicable when the iron is in the $Fe^{+2}$ or the $Fe^{+3}$ (methemoglobin) states.

Those skilled in the hemoglobin arts will recognize a wide variety of heme-binding ligands which bind to the iron of hemoglobin or methemoglobin.

For example, isocyanides such as alkyl isocyanides having 1–6 carbon atoms or phenyl isocyanides are particularly desirable heme-binding ligands for hemoglobin in the $Fe^{+2}$ state. Other suitable ligands are $O_2$ and NO.

It is generally preferred to have a single ligand bound to iron since this results in simpler measurements of the shift in allosteric forms. For example, oxyhemoglobin (glycosylated and non-glycosylated) is preferably deoxygenated by reaction with sodium dithionite or other well-known reducing agents to deoxyhemoglobin. The deoxyhemoglobin is reacted with alkylisocyanide such as n-butylisocyanide and as a result reaction with an allosteric effector site binding ligand provides a more definitive shift in equilibrium of the allosteric forms permitting determination of glycosylated hemoglobin.

Hemoglobin is oxidized to methemoglobin by art recognized techniques, Antonini and Brunoni, Hemo-

*globin and Myoglobin in Their Reactions With Ligands*, North Holland Publishing Co., Amsterdam (1971). Thus, potassium ferricyanide, sodium nitrite, aniline, and phenylhydrazine are convenient reagents for oxidizing hemoglobin to methemoglobin. Autooxidation in the presence of dyes such as methylene blue also oxidizes hemoglobin to methemoglobin.

Non-glycosylated methemoglobin is reactive with allosteric effector site binding substances described for non-glycosylated hemoglobin.

Those skilled in the hemoglobin arts will recognize a large variety of heme-binding ligands which bind with methemoglobin. These ligands include cyanate, thiocyanate, N-hydroxyacetamide, imidazole and derivatives thereof. Perutz et al., Biochemistry, 17, 3640-3652 (1978).

Other common ligands are fluoride, azide, nitrite, cyanide, water, hydroxide ammonia, acetate and formate. Imidazole at about 0.1 M is a preferred heme-binding ligand for use with methemoglobin.

In a preferred embodiment, 1 ml of a reagent which is 0.1 M imidazole, 0.2 mM potassium ferricyanide, $K_3Fe(CN)_6$, and 0.05% by volume triton x-100 (octyl phenoxypolyethoxyethanol) detergent in buffer at pH 6.8 is added to 10-20 µl of whole blood and the mixture is incubated for ten minutes.

The potassium ferricyanide oxidizes the hemoglobin to methemoglobin; the triton x-100 is a neutral detergent which lyses the cells to release hemoglobins; and the imidazole coordinates with the iron shifting equilibrium allosteric isomers to the (R) form.

The absorption spectrum of this mixture is recorded at 560 nm and 635 nm. Then 2 µl of a 0.1 M inositol hexaphosphate solution, pH 6.8 is added. The latter reagent reacts with the allosteric binding site is non-glycosylated hemoglobin and shifts equilibrium of the allosteric isomers to the (T) target form. The absorption specturm at 560 nm and 635 nm is measured again. Glycosylated hemoglobin concentration is reflected by a decrease in 560 nm absorption and increased in the 635 nm absorption.

The present invention also includes test kits for determining glycosylated hemoglobin in blood samples. The test kit includes separate or in combination a red blood cell lysing agent, an oxidizing agent for oxidizing hemoglobin to methemoglobin, a heme-binding ligand, and an allosteric site binding substance. The test kit will generally contain controls or standards. The reagents may be separate, combined into two reagents as shown in Example 1, or a single reagent as illustrated in Example 2. Those skilled in the analytical arts will recognize that these reagents may be added individually or in combination in sequence or simultaneously. A preferred test kit consists of a reagent of 0.1 M imidazole, 0.2 mM potassium ferricyanide, and 0.05% by volume triton x-100, pH 6.8, and another reagent of 0.1 M inositol hexaphosphate, pH 6.8. This kit will generally contain standards having between 0-100% glycosylated hemoglobin as well as controls having a known amount of glycosylated hemoglobin; the controls being in the normal range and some in the abnormal range.

The present invention further encompasses reagents comprising two or more of (a) a red blood cell lysing agent, (b) an oxidizing agent for oxidizing hemoglobin to methemoglobin, (c) a heme-binding ligand, and (d) an allosteric site binding substance in water or aqueous buffer as diluent, the pH being about 6 to 8, preferrably about 6.8. The combinations of (a)+(b); (a)+(b)+(c); and (a)+(b)+(c)+(d) in in diluent are preferred reagents.

The hereinafter set out examples are intended to illustrate the present invention and not limit it in spirit or scope.

EXAMPLE 1

Reagent A: 0.1 M imidazole, 0.2 mM $K_3Fe(CN)_6$, 0.05%v/v triton x-100 (octyl phenoxypolyethoxyethanol detergent), in water, pH 6.8

Reagent B: 0.1 M inositol hexaphosphate (IHP), in water, pH 6.8

To 1.0 ml of Reagent A at 25° C. add 10-20 µl whole blood, incubate 10 minutes to allow for cell lysis and oxidation of hemoglobin to methemoglobin. Record visible spectrum, 450 nm to 700 nm, specifically monitoring absorbance at 560 nm and 635 nm. Then add 2 µl Reagent B to the reaction mixture. Record another spectrum as before.

Standards are prepared by spiking whole blood with glycosylated hemoglobin.

RESULTS
Standard Curve

| % Glycosylated Hb | No IHP $A^{560nm}$ | No IHP $A^{635nm}$ | + IHP $A^{560nm}$ | + IHP $A^{635nm}$ | Normalized Difference $\frac{\Delta\Delta}{\Delta-IHP}$ |
|---|---|---|---|---|---|
| 0%   | 0.664 | 0.089 | 0.592 | 0.123 | 0.184 |
| 5%   | 0.654 | 0.086 | 0.588 | 0.120 | 0.176 |
| 10%  | 0.657 | 0.089 | 0.593 | 0.121 | 0.169 |
| 15%  | 0.658 | 0.090 | 0.596 | 0.118 | 0.158 |
| 20%  | 0.663 | 0.095 | 0.609 | 0.123 | 0.144 |
| 25%  | 0.651 | 0.091 | 0.600 | 0.117 | 0.138 |
| 50%  | 0.645 | 0.098 | 0.611 | 0.113 | 0.090 |
| 100% | 0.717 | 0.123 | 0.715 | 0.128 | 0.012 |

Calculations: $\Delta = A^{560nm} - A^{635nm}$

Normalized Difference $\pm$ IHP $= \frac{\Delta\Delta}{\Delta-IHP} = \frac{\Delta-IHP - \Delta+IHP}{\Delta-IHP}$

|  | No IHP $A^{560nm}$ | No IHP $A^{635nm}$ | + IHP $A^{560nm}$ | + IHP $A^{635nm}$ | $\frac{\Delta\Delta}{\Delta-IHP}$ |
|---|---|---|---|---|---|
| Unknown (whole blood) | 0.705 | 0.098 | 0.637 | 0.135 | 0.173 |

⟶ 8% glycosylated Hb

Check from column method (commercially available from Helena and ISOLAB)

Helena ⟶ 11.2%  ISOLAB ⟶ 7.8%

EXAMPLE 2

A single reagent addition is used by taking advantage of isosbestic points for the IHP effect to normalize for hemoglobin concentration.

Reagent C: To 1 vol. of Reagent B add 500 volumes Reagent A from Example 1

To 1.0 ml Reagent C add 10-20 µl whole blood. Incubate 10 minutes to allow for lysis, oxidation of hemoglobin to methemoglobin, and reaction of methemoglobin with imidazole and IHP. Record visible spectrum 450 nm to 700 nm, especially monitoring 476 nm, 560 nm, 635 nm, and 700 nm.

476 nm and 700 nm are isosbestic wavelength for the IHP effect.

Calculation: Normalized $\Delta\Delta = A^{560} - A^{635}/A^{476} - A^{700}$

| % Glycosylated Hemoglobin | $A^{476}$ | $A^{560}$ | $A^{635}$ | $A^{700}$ | Normalized $\Delta\Delta$ |
|---|---|---|---|---|---|
| 0% | .608 | .592 | .123 | .016 | .792 |
| 5% | .598 | .588 | .120 | .018 | .807 |
| 10% | .602 | .593 | .121 | .020 | .811 |
| 15% | .598 | .596 | .118 | .019 | .826 |
| 20% | .613 | .609 | .123 | .024 | .825 |
| 25% | .603 | .600 | .117 | .022 | .831 |
| 50% | .598 | .611 | .113 | .026 | .871 |
| 100% | .685 | .715 | .128 | .044 | .916 |
| Typical Normal Unknown | .653 | .637 | .135 | .030 | .806 5% |

RESULTS Standard Curve

EXAMPLE 3

Reagent A: 50 mM bis-tris buffer [bis-(2-hydroxethyl-)imino-tris-(hydroxymethyl)methane]; 0.05%v/v triton x-100; 1 mM n-butyl isocyanide; and 2 mg/ml sodium dithionite in water, pH 6.8

Reagent B: 2.5 mM inositol hexaphosphate (IHP), in water, pH 6.8

A purified sample of hemoglobin A is mixed with various amounts of purified glycosylated hemoglobin to give hemoglobin samples containing known amounts of glycoslated hemoglobin.

100 µl of various hemoglobin samples are placed in a cuvette and 1.0 ml of Reagent A was added. The absorbance at 530 nm and 585 nm is read after an incubation of about 2 minutes.

After the initial readings at 530 nm and 585 nm, 10 µl of Reagent B is added and after an incubation of about 1 min. the absorbance at 530 nm and 585 nm is again read.

RESULTS

| % Glycosylated Hemoglobin | No IHP $A^{530}$ | $A^{585}$ | + IHP $A^{530}$ | $A^{585}$ | $\dfrac{A^{530} - A^{585} + IHP}{A^{530} - A^{585} - IHP}$ |
|---|---|---|---|---|---|
| 0% | .529 | .153 | .369 | .261 | .287 |
| 5% | .511 | .159 | .363 | .261 | .290 |
| 10% | .489 | .174 | .368 | .260 | .343 |
| 15% | .478 | .177 | .362 | .258 | .346 |
| 20% | .487 | .191 | .377 | .268 | .368 |
| 25% | .460 | .191 | .361 | .258 | .383 |

Reagent A further containing 0.05% (triton x-100 detergent) is added to 10–20 µl of whole-blood and the analysis is run as above to determine unknown glycosylated hemoglobin.

What is claimed is:

1. A method for determining glycosylated hemoglobin in a blood sample comprising chemically or physically treating the blood sample to release glycosylated and non-glycosylated hemoglobins from red blood cells, intermixing an allosteric effector site binding substance which binds to the allosteric effector site of the non-glycosylated hemoglobin thereby changing the distribution between allosteric forms of the hemoglobins, and measuring the change.

2. The method according to claim 1 wherein the heme moiety of the hemoglobin is coordinated with a hemebinding ligand.

3. The method according to claim 1 wherein the hemoglobins are oxidized to methemoglobin.

4. The method according to claim 1 wherein the blood sample is lysed with a detergent to release hemoglobins from blood cells.

5. The method according to claim 1 wherein the change in distribution of the allosteric forms of hemoglobin is measured by absorption spectroscopy in the range of 450 nm–700 nm.

6. A method for determining glycosylated hemoglobin in a blood sample comprising:
   (a) lysing red blood cells to release glycosylated and nonglycosylated hemoglobins;
   (b) oxidizing the hemoglobins to methemoglobins and coordinating the heme moiety with a heme-binding ligand;
   (c) intermixing an allosteric effector site binding substance which binds to the allosteric effector site of the nonglycosylated hemoglobin thereby changing the distribution between allosteric forms of the hemoglobins; and
   (d) measuring the change by adsorption spectroscopy in the range of 450 nm–700 nm.

* * * * *